(12) United States Patent
Hung et al.

(10) Patent No.: US 8,211,288 B2
(45) Date of Patent: Jul. 3, 2012

(54) METHOD AND APPARATUS FOR ELECTROLYZING WATER

(75) Inventors: Yen-Con Hung, Peachtree City, GA (US); Donghwan Chung, Gangneung (KR)

(73) Assignee: University of Georgia Research Foundation, Inc., Athens, GA (US)

( * ) Notice: Subject to any disclaimer, the term of this patent is extended or adjusted under 35 U.S.C. 154(b) by 983 days.

(21) Appl. No.: 10/927,924

(22) Filed: Aug. 27, 2004

(65) Prior Publication Data

US 2005/0126928 A1 Jun. 16, 2005

Related U.S. Application Data

(63) Continuation of application No. PCT/US03/06586, filed on Mar. 3, 2003.

(60) Provisional application No. 60/361,694, filed on Mar. 6, 2002.

(51) Int. Cl.
*C02F 1/46* (2006.01)
(52) U.S. Cl. .................. 205/701; 205/746
(58) Field of Classification Search .......... 205/701, 205/746, 257, 275.1
See application file for complete search history.

(56) References Cited

U.S. PATENT DOCUMENTS

| | | | | |
|---|---|---|---|---|
| 2,535,035 | A | * 12/1950 | Briggs | 205/746 |
| 4,456,510 | A | * 6/1984 | Murakami et al. | 205/556 |
| 5,135,661 | A | 8/1992 | Patel | 210/698 |
| 5,445,722 | A | 8/1995 | Yamaguti et al. | 204/228.6 |
| 5,628,888 | A | 5/1997 | Bakhir et al. | 204/260 |
| 5,871,623 | A | 2/1999 | Bakhir et al. | 204/260 |
| 5,932,171 | A | 8/1999 | Malchesky | 422/29 |
| 5,997,717 | A | 12/1999 | Miyashita et al. | 205/466 |
| 6,033,539 | A | 3/2000 | Gablenko | 204/260 |
| 6,077,445 | A | 6/2000 | Ascolese | 210/746 |
| 6,296,744 | B1 | 10/2001 | Djeiranishvili et al. | 204/263 |
| 6,632,347 | B1 | 10/2003 | Buckley et al. | 205/620 |

FOREIGN PATENT DOCUMENTS

WO    WO 98/13304    4/1998

* cited by examiner

*Primary Examiner* — Arun S Phasge
(74) *Attorney, Agent, or Firm* — Thomas, Kayden, Horstemeyer & Risley, LLP

(57) ABSTRACT

Feed water comprising an aqueous salt solution is supplied to an anode chamber and to a cathode chamber. The feed water is cathodically electrolyzed in the cathode chamber to produce alkaline electrolyzed water (catholyte) and is anodically electrolyzed in the anode chamber to produce electrolyzed water (anolyte) whose pH is modified. A portion of alkaline catholyte from the cathode chamber is recycled back to the feed water during continuous electrolysis to provide a blend of feed water and alkaline catholyte to the anode chamber to control pH of the anodically electrolyzed water therein to provide more stable bactericidal activity thereof over time.

7 Claims, 5 Drawing Sheets

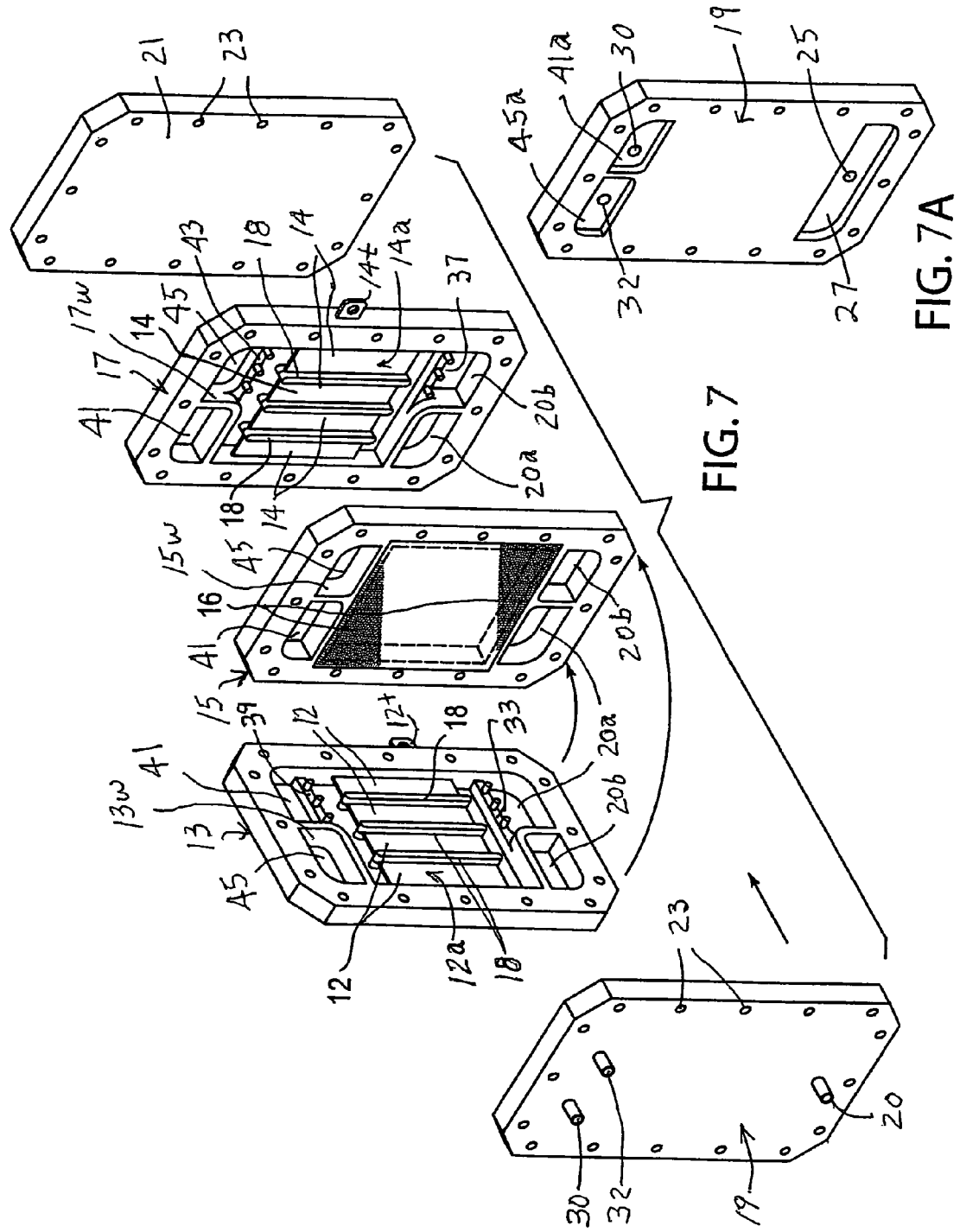

METHOD AND APPARATUS FOR ELECTROLYZING WATER

This is a continuation of international PCT application No. PCT/US03/06586 having international filing date of Mar. 3, 2003, which designates the United States, published in English under Article 21(2).

This application claims the benefits and priority of international PCT application No. PCT/US03/06586 filed Mar. 3, 2003, and U.S. Provisional Application Ser. No. 60/361,694 filed Mar. 6, 2002.

FIELD OF THE INVENTION

The present invention relates to a method and apparatus for electrolyzing water.

BACKGROUND OF THE INVENTION

Electrolyzed oxidizing (EO) water has great potential for food-related and other disinfecting processes due to its high bactericidal activity. Acidic EO water is normally generated from the anode electrode through electrolysis of a dilute aqueous NaCl solution. The $Cl^{-1}$ ions are electrochemically oxidized to $Cl_2$ gas on the anode surface, which gas is partially hydrolyzed to hypochlorous acid (HOCl) in solution phase and to other ions. The relatively high bactericidal activity of the acidic EO water is attributed to so-called active chlorine which comprises dissolved $Cl_2$, $OCl^-$ and HOCl and to the high oxidation-reduction potential (ORP) of the acidic EO water. However, the dissolved $Cl_2$ is readily evaporated or otherwise lost from the acidic EO water during storage or a treatment period, resulting in a loss of bactericidal activity over time. This loss may also affect other important properties of EO water, such as its pH, ORP, and HOCl concentration which should be known for proper use of the acidic EO water in a given service application.

SUMMARY OF THE INVENTION

The present invention provides method and apparatus for producing electrolyzed (EO) water wherein feed water comprising an aqueous salt solution is supplied to both an anode chamber and a cathode chamber. The feed water is cathodically electrolyzed in the cathode chamber to produce EO water as alkaline catholyte. The feed water is anodically electrolyzed in the anode chamber to produce electrolyzed (EO) water as anolyte whose pH is modified pursuant to the invention. A portion of the catholyte from the cathode chamber is recycled back to the feed water such that a blend of the feed water and the catholyte is supplied to the anode chamber during continuous electrolysis there. The flow rate of alkaline catholyte recycled back to the feed water is controlled to control pH of the anodically electrolyzed water (anolyte) in the anode chamber. For example, the pH of the anodically electrolyzed water (anolyte) is controlled to be above about 5, preferably between 6 and 9, to provide more stable bactericidal activity thereof over time.

The present invention is advantageous to produce anodically electrolyzed water (anolyte) at a relatively high rate at such controlled pH levels. The invention is further advantageous to produce anodically electrolyzed water with a consistent or constant active chlorine concentration regardless of the pH levels.

The advantages of the present invention will become more readily apparent from the following description taken with the following drawings.

DESCRIPTION OF THE DRAWINGS

FIG. 7 is an exploded view of an electrolyzer pursuant to an illustrative embodiment of the invention for practicing the example. FIG. 7A is a perspective view of the opposite side of the outer end frame.

DETAILED DESCRIPTION OF THE INVENTION

Figure 1:
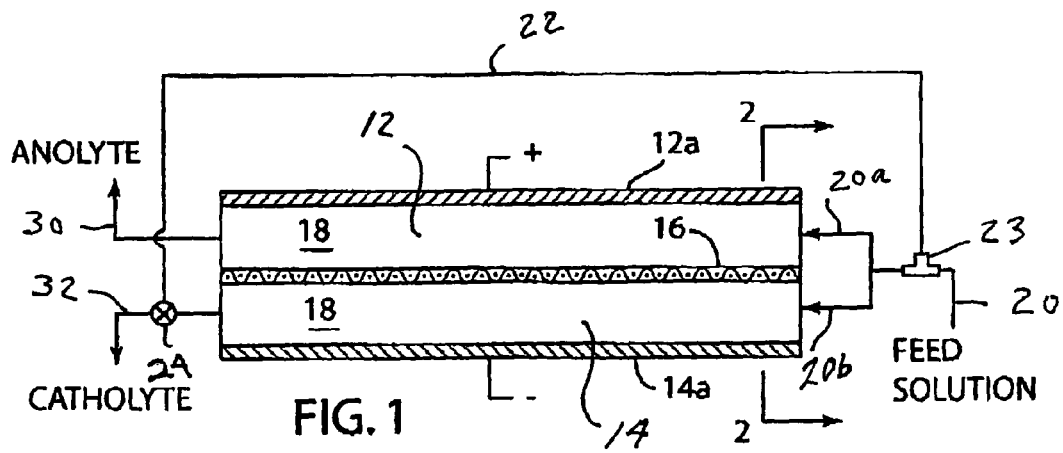
FIG. 1 is schematic longitudinal sectional view of a slab-type, membrane electrolyzer pursuant to an embodiment of the invention.
Figure 2:
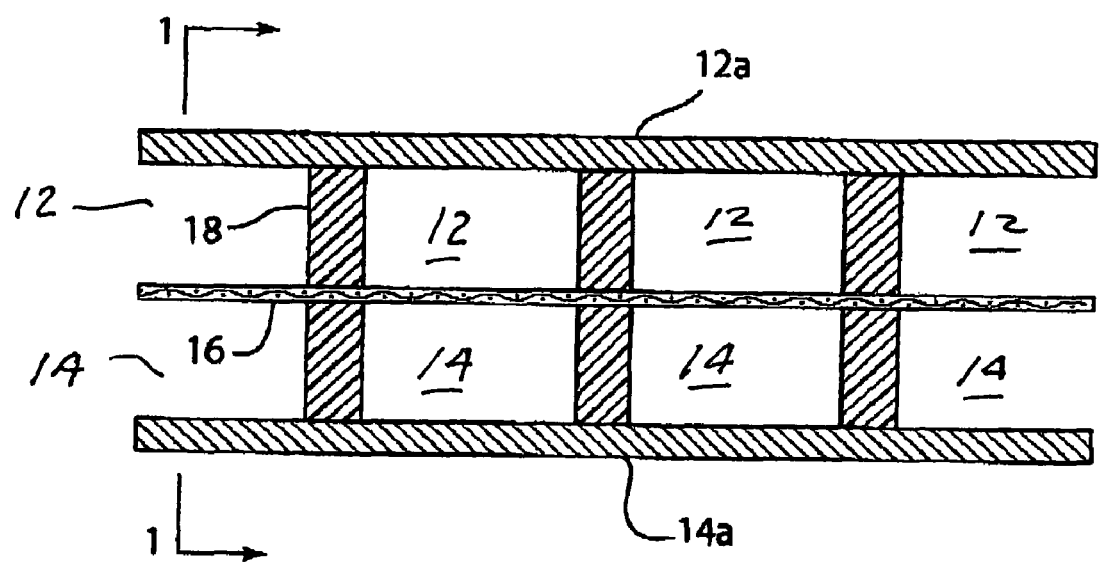
FIG. 2 is a cross-sectional view of FIG. 1 taken along lines 2-2.

Referring to FIGS. 1-2, apparatus for electrolyzing water pursuant to an illustrative embodiment of the invention is schematically shown. The apparatus includes a plurality of anode chambers 12 and cathode chambers 14 separated by a membrane 16. The chambers 12, 14 have a rectangular cross-section when in cross-sectional, FIG. 2, although the chambers can have any shape. One or more flat, plate-like anode electrodes 12a and cathode electrodes 14a (one of each electrode shown) are disposed in the anode chambers and cathode chambers, respectively. The anode and cathode electrodes can comprise titanium or titanium coated with a precious metal, such as platinum, or they can comprise any other suitable electrode material. The membrane 16 can comprise either a non-ion selective separator membrane comprising, for example, non-woven polyester fabric, or an ion selective permeable membrane comprising, for example, a perfluorosulfonate ionomer. When the feed water to be electrolyzed comprises a dilute aqueous NaCl salt solution, the membrane allows $Na^+$ ions to move toward the cathode electrode 14a from the anode chamber 12 and $Cl^{-1}$ ions to move toward the anode electrode 12a from the cathode chamber 14. The membrane 16 is spaced between the electrodes by electrically insulating plastic spacers 18. The electrodes are connected to a conventional electrical power supply (not shown) to thereby provide an electrochemical cell for electrolyzing water.

The feed water to be electrolyzed typically comprises a dilute aqueous NaCl solution, such as 0.01% to 25% by weight NaCl solution, although the invention can be practiced to electrolyze other aqueous solutions of KCl, $MgCl_2$ and other salts.

Referring to the embodiment of FIGS. 1-2, the feed water (designated "feed solution" in FIGS. 1, 5, and 6) is supplied to both the anode chambers 12 and cathode chambers 14 via a feed water supply conduit 20 that is branched to have an anode supply conduit section 20a and cathode supply section 20b from the common conduit 20. The anode supply water conduit section 20a supplies the feed water only to anode chambers 12 via a manifold (not shown) that communicates with each of the plurality of anode chambers 12 as described below for the example. The cathode supply water conduit section 20b supplies the feed water only to cathode chambers 14 via a manifold (not shown) that communicates with each of the plurality of cathode chambers 14 as described below for the example.

The feed water is cathodically electrolyzed in the cathode chambers 14 to produce EO water as alkaline catholyte. The feed water is anodically electrolyzed in the anode chambers 12 to produce electrolyzed (EO) water as anolyte whose pH is modified pursuant to the invention. The pH-modified, anodically electrolyzed water (anolyte) is discharged from the anode chambers 12 by way of an anolyte discharge conduit 30 for collection and use. The cathodically electrolyzed water (catholyte) is discharged from the cathode chambers 14 by way of a catholyte discharge conduit 32 for collection and use and for recycling back to the anode chambers 12 as described below pursuant to an illustrative embodiment of the invention.

Pursuant to an illustrative embodiment of the invention, the apparatus includes catholyte return conduit 22 or other means for returning a portion of the alkaline catholyte from the cathode chamber 14 to the feed water in supply conduit 20 to provide a blend of the feed water and the catholyte to the anode chambers 12. The blend of feed water and catholyte is also provided to the cathode chambers 14. The flow rate of feed water in the cathode chambers 14 typically is substantially equal to the flow rate of the blend of feed water and recycled catholyte in the anode chambers 12, although different flow rates can be provided through the chambers 12, 14. A conventional valve 24 made of PVC is provided between the catholyte discharge conduit 32 and the catholyte return conduit 22 to control the flow rate of catholyte returned to the feed water. The return conduit 22 can be communicated to the supply conduit 20 by use of a conventional T-junction 23 or any other suitable pipe connecting means. The flow rate of the alkaline catholyte recycled or returned from the catholyte discharge conduit 32 to the feed water in supply conduit 20 is controlled to control pH of the anodically electrolyzed water (anolyte) in anode chamber 12 to a pH value effective to provide more stable bactericidal activity thereof over time. For example, the pH of the anodically electrolyzed water discharged from anode chambers 12 is controlled above 5, and preferably between 6 to 9, to provide more stable bactericidal activity over time where the active chlorine concentration of the anodically electrolyzed water (anolyte) is generally constant at all pH values in that range as will be discussed below in connection with the Example.

Figure 5:
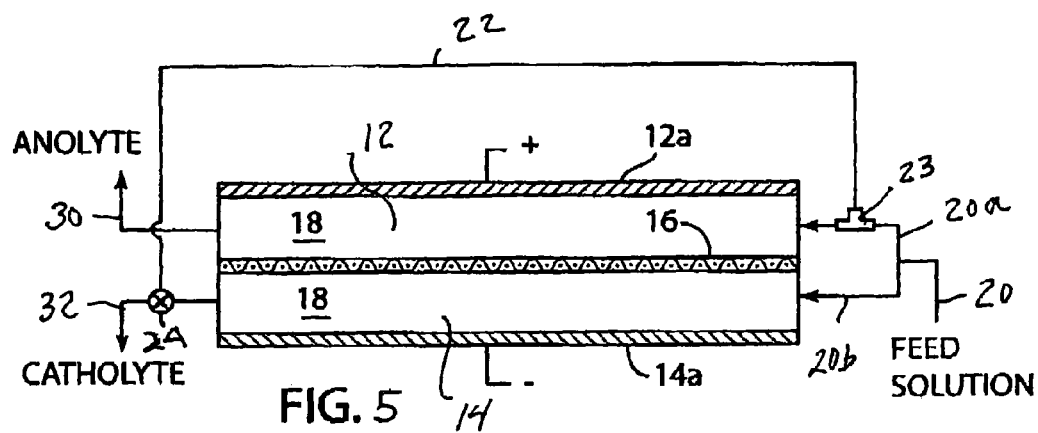
FIG. 5 is a schematic view of an electrolyzer pursuant to another embodiment of the invention.
Figure 6:
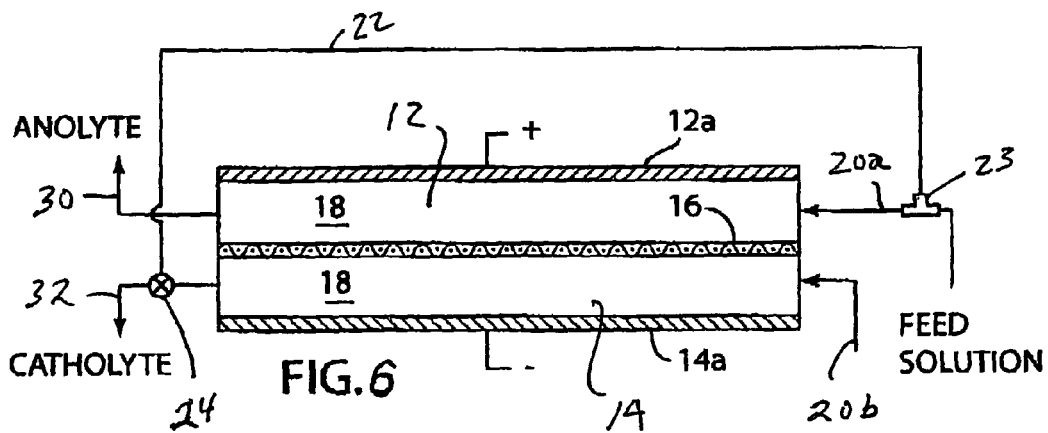
FIG. 6 is a schematic view of an electrolyzer pursuant to still another embodiment of the invention.

FIG. 5 illustrates another embodiment of the invention wherein the catholyte return conduit 22 is communicated only to the supply branch 20a so as to supply the blend of feed water and recycled catholyte to the anode chambers 12 only. That is, the anode chambers 12 receive the blend of feed water and catholyte, while the cathode chambers 14 receive only feed water (sans recycled catholyte). FIG. 6 illustrates still another embodiment of the invention wherein a separate feed water supply conduit 20a, 20b is provided to the anode chambers 12 and to the cathode chambers 14, and the catholyte return conduit 22 is communicated only to the supply conduit 20a to supply the blend only to the anode chambers 12.

The following Example is offered to further illustrate and not limit the invention.

EXAMPLE

Anodically electrolyzed water (anolyte) was generated at different pH values using apparatus functioning as shown and described for FIG. 1 and shown in more detail in FIGS. 7, 7A. In FIGS. 7 and 7A, the side edges of a flat anode electrode 12a are mounted in a plastic frame 13 as shown, the membrane 16 is mounted (glued) on a plastic frame 15, and the side edges of a flat cathode electrode 14a are mounted in a plastic frame 17. The membrane 16 is shown broken away in FIG. 7 for convenience but spans the entire area between the membrane segments shown. The spacers 18 are glued on the opposite flat major surfaces of the anode electrode 12a and cathode electrode 14a as shown. The frames 13, 15, 17 are adapted to be stacked side-by-side with end frames 19, 21 to form the electrolyzer. The frames includes holes 23 that are aligned when the frames are assembled to receive fasteners to hold and seal mating surfaces of the frames together. The assembled frames forming the electrolyzer were oriented vertically for experiments described below, but the orientation can be any other orientation than vertical.

When assembled, the end frame 19 includes feed water supply conduit 20 on its exterior side communicated in flow relation to a passage 25 therethrough to a manifold 27 on its interior side, FIG. 7A. The manifold 27 is communicated in flow relation to passages 20a, 20b that correspond to anode supply water conduit section 20a and cathode supply water conduit section 20b of FIG. 1 and that distribute feed water to the anode chambers 12 and to the cathode chambers 14, respectively. The feed water flows from the manifold 27 through passage 20a and channel 33 in frame 13 to the anode chambers 12, which are defined by flat anode electrode 12a, spacers 18, membrane 16 and sides of frame 13. The feed water flows through passage 20b and channel 37 in frame 17 to the cathode chambers 14, which are defined by flat cathode electrode 14a, spacers 18, membrane 16 and sides of frame 17, the cathode chambers 14 being on the opposite side of the membrane 16 from the anode chambers 12. The anolyte flows along and from the anode chambers 12 through channel 39 between the spacer posts shown to anolyte discharge passage 41, which is communicated in flow relation to anolyte discharge recess 41a on the interior of end frame 19 and then to anolyte discharge conduit 30. The catholyte flows along and from the cathode chambers 14 through channel 43 between the spacer posts shown to catholyte discharge passage 45, which is communicated in flow relation to catholyte discharge recess 45a on the interior of end frame 19 and then to catholyte discharge conduit 32. The anolyte discharge passage 41 is separated from the catholyte discharge passage 45 by walls 13w, 15w, 17w on frames 13, 15, 17, the walls being sealed to one another when the frames are assembled. The anode electrode 12a and cathode electrode 14a include respective integral positive and negative terminal tabs 12t and 14t embedded in and extending out of side of the frames where the electrical power is supplied. End frame 19, frames 13, 15, 17, and end frame 21 were stacked together to form the electrolyzer. The catholyte return conduit 22 (not shown in FIG. 7) was connected to catholyte discharge conduit 32 and to the feed water supply conduit 20 as shown in FIG. 1. The invention envisions stacking additional frames 13, 15, and 17 together to increase production rate of electrolyzed water.

The feed water comprised an aqueous 0.1 weight % NaCl solution. The feed water was electrolyzed at a cell voltage of 10V and at a temperature of 24 degrees C. plus or minus 1 degree C. The feed water was supplied to the cathode chambers 14 collectively at a flow rate of 1.0 L/minute. The blend of feed water and catholyte was supplied to the anode chambers 14 collectively at a flow rate of 1.0 L/minute. Alkaline catholyte (pH above 11) from the cathode chambers 14 was recycled or returned to the feed water (at T-junction 23 in FIG. 1) at various recycle ratios R where R=recycle catholyte flow rate/cathode chamber flow rate and where, as mentioned, the flow rate through cathode chambers 14 was 1.0 L/minute. For example, an R=0 indicates that there is 0% recycling of catholyte to the feed water and an R=1 indicates that there is 100% recycling of catholyte to the feed water at junction 23.

Figure 3:
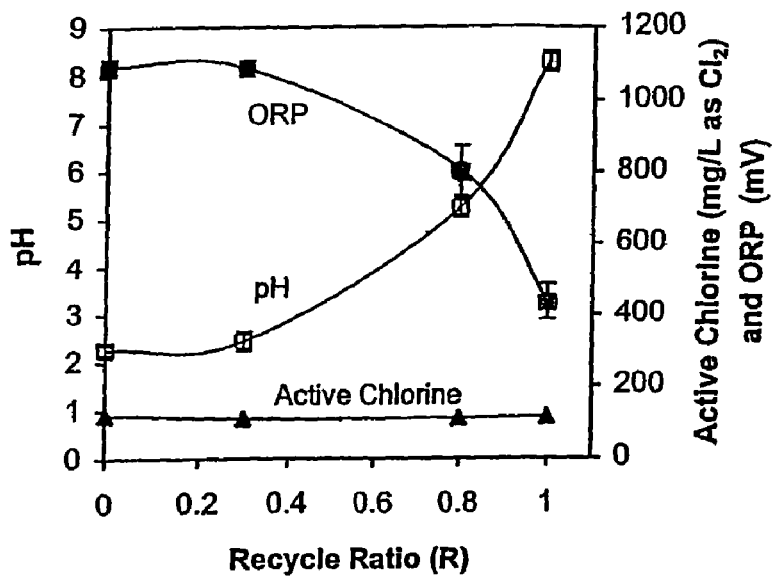
FIG. 3 is a graph of pH, ORP, and the concentration of active chlorine of anodically electrolyzed water generated at various recycle ratios, R, where R=catholyte recycle flow rate/cathodic chamber flow rate.

FIG. 3 is a graph of pH, ORP, and the concentration of active chlorine of the anodically electrolyzed water (anolyte) generated at the various recycle ratios, R=0.3, 0.8 and 1.0. It is apparent from FIG. 3 that the pH of the anodically electrolyzed water increased as the recycle ratio increased, while the ORP decreased as the recycle ratio increased. Importantly, it is also apparent from FIG. 3 that the active chlorine concentration of the anodically electrolyzed water (anolyte) is substantially consistent or constant over the range of controlled pH values of the anodically electrolyzed water. The active chlorine comprised dissolved $Cl_2$ and HOCl and was measured using a total chlorine test kit available form Hach Co., Ames, Iowa. The concentrations of $Cl^{-1}$ ions were measured using a $Cl^{-1}$ test kit available from Hach Co. based on the silver nitrate method. The pH and ORP were measured using a digital pH/ORP meter available as Accumet model 15 from Fisher Scientific Co., Fairlawn, N.J.

Figure 4:
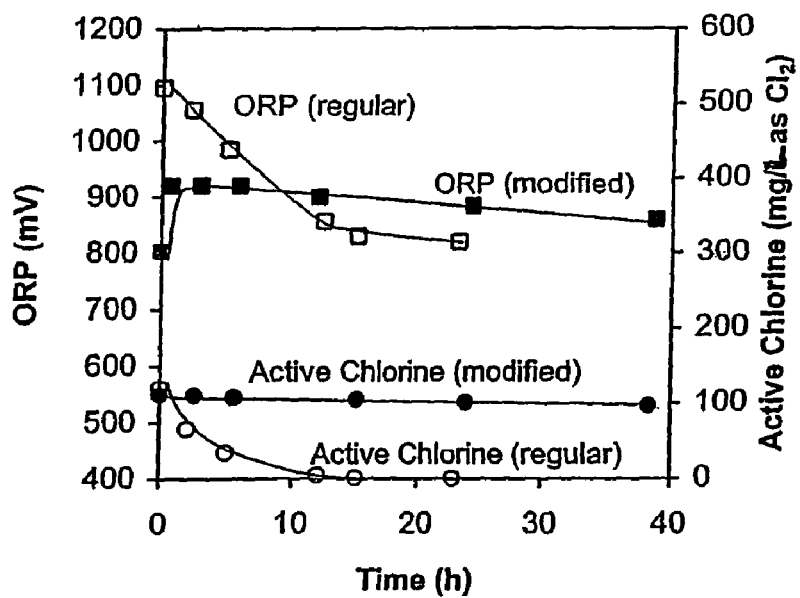
FIG. 4 is a graph comparing stability of ORP and active chlorine of anodically electrolyzed water having a pH=5.2 generated at a catholyte recycle ratio R=0.8 pursuant to the invention and of anodically electrolyzed water conventionally generated at pH of 2.3 (generated without recycle of catholyte).
Figure 8A:
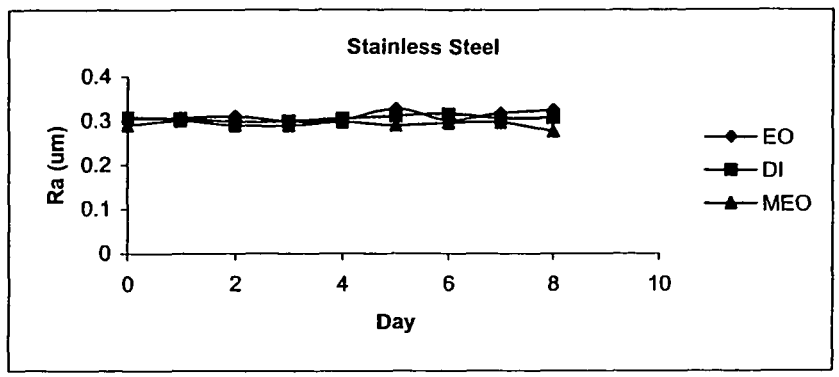
FIGS. 8A, 8B, 8C, and 8D are graphs of average surface roughenss Ra versus time in days for stainless steel, carbon steel, aluminnum, and copper immersed in different test waters.
Figure 8B:
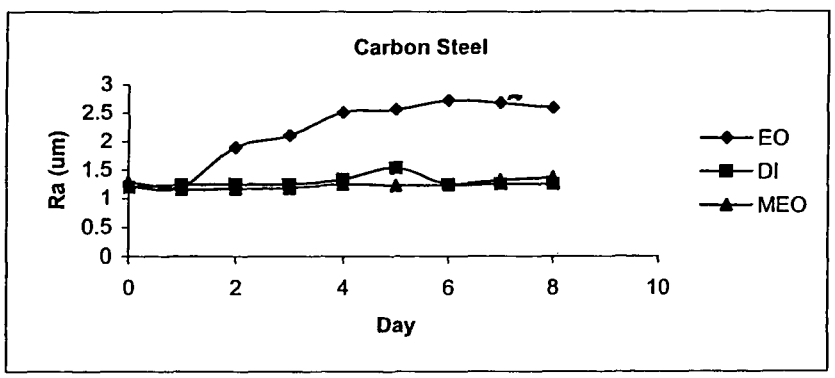
Figure 8C:
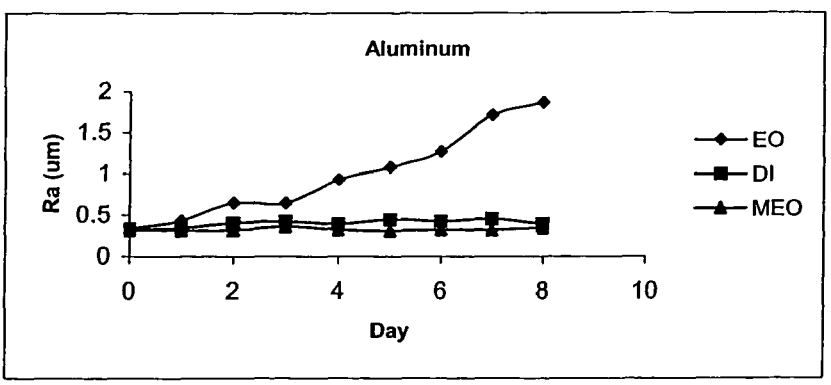
Figure 8D:
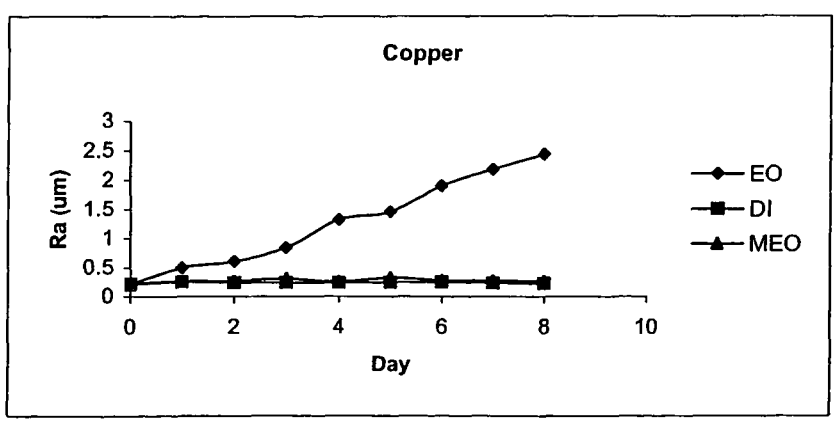

FIG. 4 compares stability of active chlorine and ORP of anodically electrolyzed water (anolyte) produced pursuant to the invention at a pH of 5.2 and R=0.8 and designated "ORP (modified)" or "active chlorine (modified)" in FIG. 4. For comparison, the stability of anodically electrolyzed water (anolyte) produced at pH 2.3 by conventional electrolysis apparatus similar to that of FIG. 1 but without catholyte recycling to the anode chambers (feed water flow rate of 1 L/minute to each of the anode chambers and cathode chambers) is shown in FIG. 4. In FIG. 4, the designations "active chlorine (regular)" and "ORP (regular)" are used to designate the anodically electrolyzed water produced using the conventional electrolysis apparatus.

Stability of the anodically electrolyzed water (anolyte) was determined at various times intervals over a period of 38 hours while the water was stored in a container open to ambient air at 25 degrees C. and agitated by a magnetic stirring at 250 rpm.

It is apparent that the concentration of active chlorine of anodically electrolyzed water (anolyte) produced pursuant to the invention was substantially constant at about 100-110 mg/L as $Cl_2$ over a storage time up to 38 hours at 25 degrees C. In contrast, the concentration of active chlorine of anodically electrolyzed water (anolyte) produced by the conventional electrolysis apparatus decreased rapidly to 0 over a time period of 15 hours. The ORP of anodically electrolyzed water produced pursuant to the invention remained greater than that of the anodically electrolyzed water produced by conventional electrolysis over a time period of 23 hours.

The bactericidal activity of anodically electrolyzed water produced pursuant to the invention and the "regular" anodically electrolyzed water at pH 2.3 was evaluated. In particular, a five strain mixture of E. coli O157:H7 was subjected to deionized water (control), the "regular" anodically electrolyzed water at pH 2.3, and two anodically electrolyzed waters produced pursuant to the invention at pH 5.2 and pH 8.3, and was incubated at 23 degrees C. for 30 seconds. The anodically electrolyzed water was appropriately diluted using deionized water and tested at two active chlorine levels (i.e. 24 and 50 mg/$Cl_2$). The initial production of E. coli O157:H7 was 8.03 $log_{10}$ CFU/ml.

Table 1 below shows that the anodically electrolyzed water (anolyte) generated at pH 5.2 and 8.3 pursuant to the invention achieved 8 log reductions of the E. coli strains after 30 second treatment at 25 mg/$Cl_2$ and 50 mg/$Cl_2$ active chlorine levels and is equally effective as the "regular" anodically electrolyzed water.

TABLE 1

Bactericidal activities of regular and modified EO water against E. coli O157:H7 after 30 sec-treatments

| Treating solution | Active Chlorine (mg/L as $Cl_2$) | Surviving population ($log_{10}$CFU/ml) |
|---|---|---|
| Deionized water (control) | 0 | 8.01 ± 0.04 |
| Regular EO water (pH 2.3) | 50 | ND[a] |
| | 25 | ND |
| Modified EO water (pH 5.2) | 50 | ND |
| | 25 | ND |
| Modified EO water (pH 8.3) | 50 | ND |
| | 25 | ND |

[a]Negative by an enrichment procedure and no detectable survivors by a direct plating procedure.

The invention can be practiced to produce anodically electrolyzed water for use in any hygiene-sensitive service application for on-site generation of stable and strong disinfecting solution. The applications include washing food surfaces, such as poultry products and fresh produce, as well as cleaning food contact surfaces such as food processing equipment, food handling facilities, utensils, and hands in food industries, restaurants, service centers, and homes. The anodically electrolyzed water produced pursuant to the invention also is useful for cleaning other surfaces such as floors, carpets, and shower curtains to name a few to reduce cross-contamination in medical/dental services, homes, and nursing care facilities. The invention is also suited for agricultural applications to replace other chemical pesticides and fungicides.

The invention is advantageous to produce anodically electrolyzed water at a relatively high rate at all controlled pH values described above, as compared to production rates achievable using serial electrolysis apparatus. Moreover, the active chlorine concentration of the anodically electrolyzed water produced pursuant to the invention is substantially constant over the range of controlled pH values (see FIG. 2) in contrast to the variable active chlorine produced using serial electrolysis apparatus wherein the active chlorine concentration decreases as the pH of the anodically electrolyzed water increases.

The recycle-electrolysis method of the invention provides a novel means for generating electrolyzed water with a more stable bactericidal activity than the regular electrolyzed water. The method of the invention also has a higher production yield (less by-product (catholyte)) than the regular electrolysis methods. Recycling of alkaline catholyte to the anode chamber pursuant to the invention increases the pH of the electrolyzed water (anolyte) during continuous electrolysis of a dilute salt solution. At a sufficiently high pH value (e.g. pH greater than 5), the evaporation of dissolved $Cl_2$, which is a main cause of bactericidal activity reduction of regular acidic electrolyzed water, can be minimized, while the fraction of HOCl, which is the most effective chlorine species in electrolyzed water, is maintained.

Anodically electrolyzed water produced pursuant to the invention is less corrosive than anodically electrolyzed water produced by conventional electrolysis apparatus as described in the Example above. Corrosion tests were conducted using ASTM Standard G48-99 (Standard Test Methods for pitting corrosion and crevice corrosion resistance of stainless steels and related alloys by use of ferric chloride solution, 1999) and ASTM G31-72 (Standard Test Method for laboratory immersion corrosion testing of metals, 1999). ASTM A-36 medium carbon steel, 110 copper, 3003-H14 aluminum, and Type 304 stainless steel coupons were immersed in deionized water, regular anodically electrolyzed water (designated EO water) made as described in the Example above, and anodically electrolyzed water made pursuant to the invention (designated MEO water) for a period of 8 days. The EO water and MEO water are characterized by their pH, ORP (mv), and Chlorine (ppm) in the Table 2 below.

TABLE 2

|  | pH | ORP (mv) | Chlorine (ppm) |
|---|---|---|---|
| Regular EO water | 2.44 | 1038 | 49 |
| MEO water | 6.19 | 773 | 50 |

Each day, coupons were removed from the testing solution and average surface roughness (Ra) and weight were determined using a surface roughness meter (Hommel Tester T1000), Hommel America, New Britain Conn. 06051, and a balance, respectively. After the measurements, the coupons were then re-immersed in a fresh test solution. In general, the Ra value will increase (surface becomes rough) with time if the test solution is corrosive. Annual corrosion rate was calculated based on the mass loss of each coupon after 8 days. If the calculated annual corrosion rate (mm/year) is less than 0.02, the material is considered "Outstanding" in corrosion resistance. The rating will decrease to "Excellent", "Good", "Fair", "Poor", and "Unacceptable" if annual the corrosion rates are in the range of "0.02 to 0.1", "0.1 to 0.5", "0.5 to 1.0", "1.0 to 5.0", and "larger than 5.0", respectively.

As demonstrated in the attached FIGS. 8A through 8D, Ra values of all four metals tested remained unchanged if immersed in deionized water (DI) and the EO water made pursuant to the invention (designated MEO in FIGS. 8A-8D). However, Ra values increased with test time for carbon steel, aluminum, and copper immersed in the regular EO water. Calculated annual corrosion rates indicated that the MEO water made pursuant to the invention yielded an "Outstanding" corrosion resistance rating with respect to copper, aluminum, and stainless steel, whereas the regular EO water yielded only a "Good" corrosion resistance rating with respect to copper and aluminum. The annual corrosion rates for stainless steel (S-st), carbon steel (C-st), aluminum (Al), and copper (Cu) are set forth in Table 3 below:

TABLE 3

| | Annual Corrosion Rate (mm/yr) | | |
|---|---|---|---|
| | EO | DI | MEO |
| S-st | 0.0033 | 1.72E−05 | 0.0047 |
| C-st | 0.5754 | 0.0021 | 0.2856 |
| Al | 0.3228 | −9.06E−05 | −0.00136 |
| Cu | 0.4636 | 0.0015 | 0.0068 | where for stainless steel (S-st), the value $1.72E\text{-}05 = 1.72 \times 10^{-5}$ and for aluminum, the value $-9.06E\text{-}05 = -9.06 \times 10^{-5}$ mm/yr.

Although the invention has been described in terms of specific embodiments thereof, those skilled in the art will appreciate that the invention is not limited and changes and modifications can be made therein within the scope of the invention as set forth in the appended claims.

We claim:

1. A method of making electrolyzed water, comprising supplying unelectrolyzed feed water comprising an aqueous salt solution to an anode chamber where anodically electrolyzed water is produced and to a cathode chamber where cathodically electrolyzed alkaline water is produced, and returning a portion of the cathodically electrolyzed water to only the unelectrolyzed feed water supplied to the anode chamber to provide a blend of the unelectrolyzed feed water and the cathodically electrolyzed water to the anode chamber to control pH of the anodically electrolyzed water wherein the flow rate of the blend in the anode chamber is substantially equal to the flow rate of the unelectrolyzed feed water in the cathode chamber.

2. The method of claim 1 wherein said pH is controlled above 5.

3. The method of claim 2 wherein said pH is controlled between 6 and 9.

4. The method of claim 2 wherein the active chlorine concentration of said anodically electrolyzed water is generally constant over at said pH above 5.

5. The method of claim 1 wherein the pH of said anodically electrolyzed water is controlled to provide a concentration of active chlorine therein that is substantially constant over a storage time up to 38 hours at 25 degrees C. in an open container with agitation.

6. A method of making electrolyzed water, comprising supplying unelectrolyzed feed water comprising an aqueous salt solution to an anode chamber where anodically electrolyzed water is produced and to a cathode chamber where cathodically electrolyzed alkaline water is produced, and returning a portion of the cathodically electrolyzed water to the unelectrolyzed feed water supplied to both the anode chamber and the cathode chamber to provide a blend of the unelectrolyzed feed water and the cathodically electrolyzed water to the anode chamber and to the cathode chamber, said blend supplied to the anode chamber being effective to control pH of the anodically electrolyzed water, wherein the flow rate of the blend in the cathode chamber is substantially equal to the flow rate of the blend in the anode chamber.

7. The method of claim 6 wherein the pH of said anodically electrolyzed water is controlled to provide a concentration of active chlorine therein that is substantially constant over a storage time up to 38 hours at 25 degrees C. in an open container with agitation.

* * * * *